US011512809B2

United States Patent
Oginski et al.

(10) Patent No.: US 11,512,809 B2
(45) Date of Patent: Nov. 29, 2022

(54) ROTATABLE CONNECTION WITH ROTATIONAL ANGLE LIMITATION

(71) Applicant: Ondal Medical Systems GmbH, Hünfeld (DE)

(72) Inventors: Stefan Oginski, Fulda (DE); Ronny Bauditz, Suhl (DE); Andreas Göbel, Eiterfeld (DE); Annika Euler, Hünfeld (DE)

(73) Assignee: Ondal Medical Systems GmbH, Hünfeld (DE)

( * ) Notice: Subject to any disclaimer, the term of this patent is extended or adjusted under 35 U.S.C. 154(b) by 714 days.

(21) Appl. No.: 16/380,064

(22) Filed: Apr. 10, 2019

(65) Prior Publication Data
US 2019/0301666 A1    Oct. 3, 2019

Related U.S. Application Data

(62) Division of application No. 14/695,372, filed on Apr. 24, 2015, now Pat. No. 10,260,673.

(30) Foreign Application Priority Data

Apr. 24, 2014    (EP) .................................... 14001479

(51) Int. Cl.
*F16M 11/20*    (2006.01)
*F16M 11/08*    (2006.01)
(Continued)

(52) U.S. Cl.
CPC ......... *F16M 11/2007* (2013.01); *A61B 50/10* (2016.02); *A61B 50/20* (2016.02);
(Continued)

(58) Field of Classification Search
CPC ............... F16M 11/08; F16M 11/2007; F16M 11/20147; F16M 2200/024; F16M 13/027;
(Continued)

(56) References Cited

U.S. PATENT DOCUMENTS 1,634,922 A    7/1927    Stubblebine et al.
3,133,743 A    11/1962    Mullin
(Continued)

FOREIGN PATENT DOCUMENTS

CN    102762877    2/2016
DE    3808327    9/1988
(Continued)

OTHER PUBLICATIONS

U.S. Appl. No. 16/379,233, filed Apr. 9, 2019, Oginski et al.
European Search Report received for U.S. Patent Application No. EP 14001479, dated Oct. 12, 2014.

*Primary Examiner* — Matthew R McMahon
(74) *Attorney, Agent, or Firm* — Workman Nydegger

(57) ABSTRACT

A rotatable connection for a stand apparatus to be arranged in an operating room and including an adaptable stop mechanism which can be arranged between a first connection component and a second connection component mounted rotatably around a rotational axis relative to the first connection component and is configured to define at least two different relative rotational angles of the connection components or at least two different rotational ranges is provided. A carrier system or a stand apparatus having such a rotatable connection is also provided.

14 Claims, 8 Drawing Sheets

Figure 1:
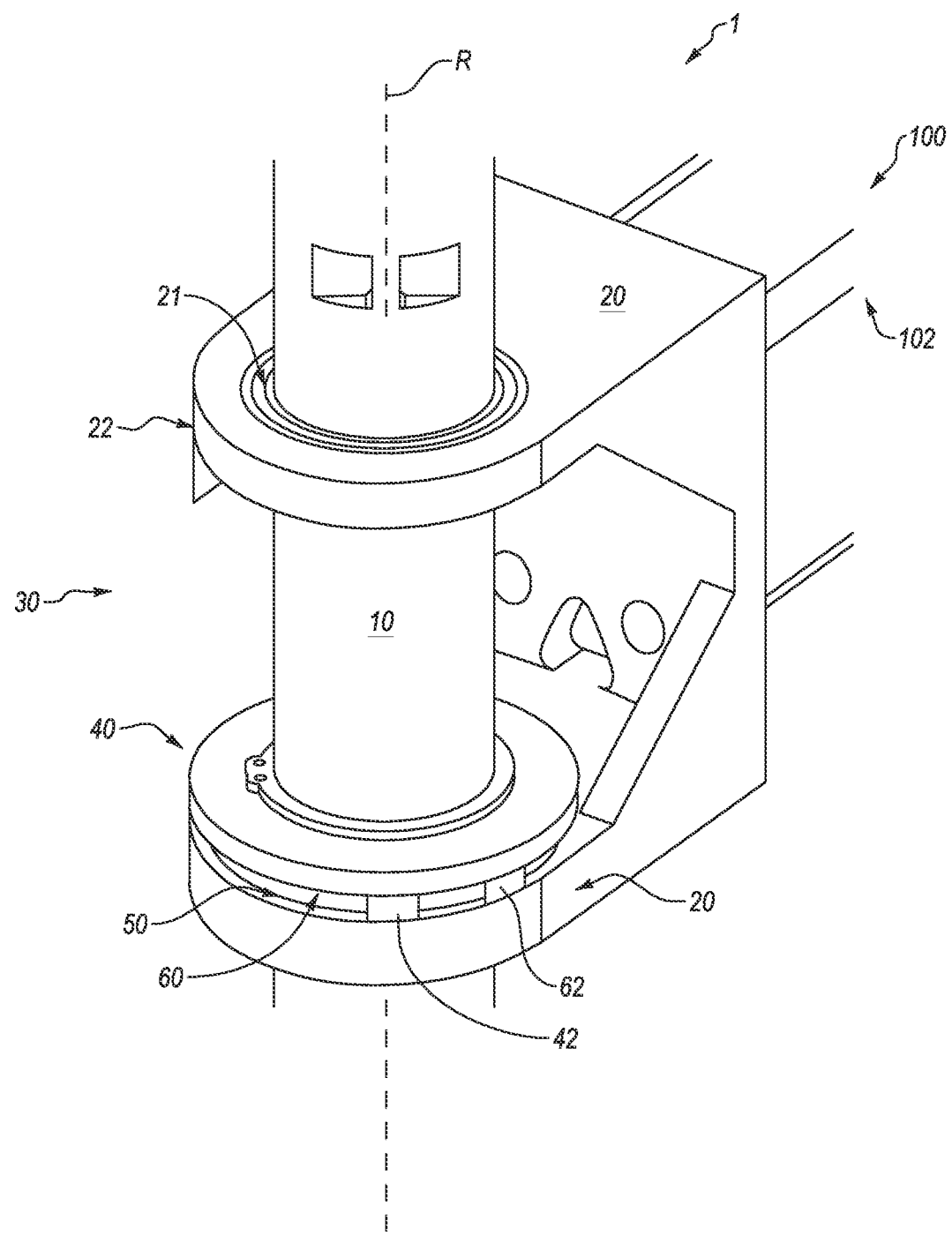

(51) Int. Cl.
  *F16M 13/02* (2006.01)
  *A61B 50/10* (2016.01)
  *A61B 50/20* (2016.01)
  *A61B 50/24* (2016.01)
  *F16C 11/10* (2006.01)

(52) U.S. Cl.
  CPC .............. *A61B 50/24* (2016.02); *F16C 11/10* (2013.01); *F16M 11/08* (2013.01); *F16M 11/2014* (2013.01); *F16M 13/027* (2013.01); *F16M 2200/024* (2013.01); *Y10T 403/32336* (2015.01); *Y10T 403/32549* (2015.01)

(58) Field of Classification Search
  CPC ..... Y10T 403/32336; Y10T 403/32549; Y10T 403/32557; Y10T 403/32975; F16C 11/10
  See application file for complete search history.

(56) References Cited

U.S. PATENT DOCUMENTS

| | | | |
|---|---|---|---|
| 3,713,618 A | 1/1973 | Hendrickson et al. | |
| 4,303,135 A | 12/1981 | Benoit | |
| 4,587,908 A | 5/1986 | DeBruyn | |
| 4,673,154 A | 6/1987 | Karapita | |
| 4,772,246 A | 9/1988 | Wenzel | |
| 4,938,094 A | 7/1990 | Cochard | |
| 5,123,768 A | 6/1992 | Franklin | |
| 5,685,661 A | 11/1997 | Marka et al. | |
| 5,720,570 A | 2/1998 | Cole et al. | |
| 6,030,103 A | 2/2000 | Gampe et al. | |
| 6,079,949 A | 6/2000 | Litvin | |
| 6,226,068 B1 | 5/2001 | Arcykiewicz et al. | |
| 6,234,259 B1 | 5/2001 | Kuckes et al. | |
| 6,471,363 B2 | 10/2002 | Howell et al. | |
| 6,633,328 B1 | 10/2003 | Byrd et al. | |
| 6,698,704 B2 | 3/2004 | Kuhn | |
| 6,817,585 B2 | 11/2004 | Wagner et al. | |
| 6,866,410 B2 | 3/2005 | Jesurun et al. | |
| 6,899,442 B2 | 5/2005 | Howell et al. | |
| 7,216,726 B2 | 5/2007 | Swietlik et al. | |
| 7,452,088 B2 | 11/2008 | Brester et al. | |
| 7,455,328 B2 | 11/2008 | Chelchowski et al. | |
| 7,559,518 B2 | 7/2009 | Ye | |
| 7,591,446 B2 | 9/2009 | Istas et al. | |
| 7,635,234 B2 | 12/2009 | Schindler et al. | |
| 7,726,823 B2 | 6/2010 | Rus et al. | |
| 7,753,330 B2 | 7/2010 | Brief | |
| 7,938,205 B2 | 5/2011 | Puttman | |
| 8,056,874 B2 | 11/2011 | Goodwin et al. | |
| 8,070,331 B2 | 12/2011 | Gull et al. | |
| 8,209,816 B2 | 7/2012 | Heger et al. | |
| 8,262,311 B2 | 9/2012 | Trice | |
| 8,591,444 B2 | 11/2013 | Bejarano et al. | |
| 9,022,339 B2 | 5/2015 | Borg et al. | |
| 9,239,127 B2 | 1/2016 | Kronung | |
| 9,280,037 B2 | 3/2016 | Leblanc et al. | |
| 9,719,560 B2 | 8/2017 | Dreizler | |
| 9,869,343 B2 | 1/2018 | Oginski et al. | |
| 10,247,352 B2 | 4/2019 | Oginski et al. | |
| 10,253,806 B2 | 4/2019 | Oginski et al. | |
| 2005/0006542 A1 | 1/2005 | Henning et al. | |
| 2005/0121578 A1 | 6/2005 | Asamarai et al. | |
| 2005/0242261 A1 | 11/2005 | Brahler et al. | |
| 2006/0285915 A1 | 12/2006 | Dellach et al. | |
| 2009/0072106 A1 | 3/2009 | Zheng | |
| 2009/0213596 A1 | 8/2009 | Gull et al. | |
| 2009/0245924 A1 | 10/2009 | Whitling et al. | |
| 2011/0314637 A1 | 12/2011 | Bejarano et al. | |
| 2012/0014744 A1 | 1/2012 | Lin | |
| 2012/0059274 A1 | 3/2012 | Zoth et al. | |
| 2012/0228454 A1 | 9/2012 | Krönung | |
| 2013/0189019 A1 | 7/2013 | Kotula et al. | |
| 2014/0105670 A1 | 4/2014 | Plomteux | |
| 2014/0314538 A1 | 10/2014 | Carter et al. | |
| 2015/0308611 A1 | 10/2015 | Oginski et al. | |
| 2015/0366627 A1 | 12/2015 | Oginski et al. | |
| 2015/0377283 A1 | 12/2015 | Oginski et al. | |
| 2016/0102702 A1 | 4/2016 | Lang et al. | |
| 2016/0102802 A1 | 4/2016 | Oginski et al. | |
| 2016/0281915 A1 | 9/2016 | Bowman et al. | |
| 2017/0304022 A1 | 10/2017 | Oginski et al. | |
| 2020/0158278 A1 | 5/2020 | Daugirdas | |

FOREIGN PATENT DOCUMENTS

| | | |
|---|---|---|
| DE | 4306802 | 8/1994 |
| DE | 102008011129 | 8/2009 |
| EP | 0392303 | 10/1990 |
| EP | 0614037 | 3/1994 |
| EP | 1473473 | 9/2006 |
| EP | 2096349 | 9/2009 |
| EP | 2325541 | 5/2011 |
| EP | 2937617 | 10/2015 |
| EP | 2937618 | 10/2015 |
| EP | 2937619 | 10/2015 |
| FR | 1341061 | 10/1963 |

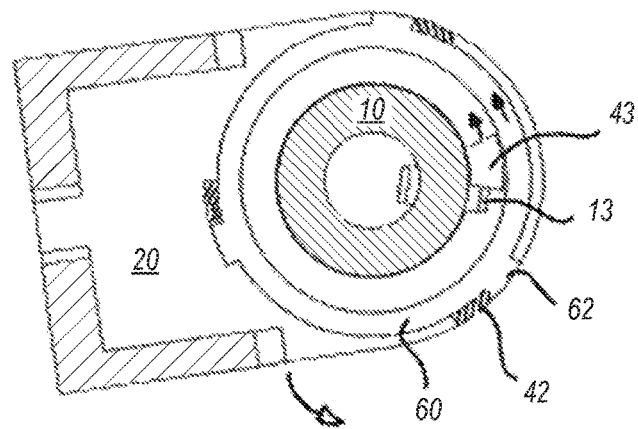
FIG. 4A
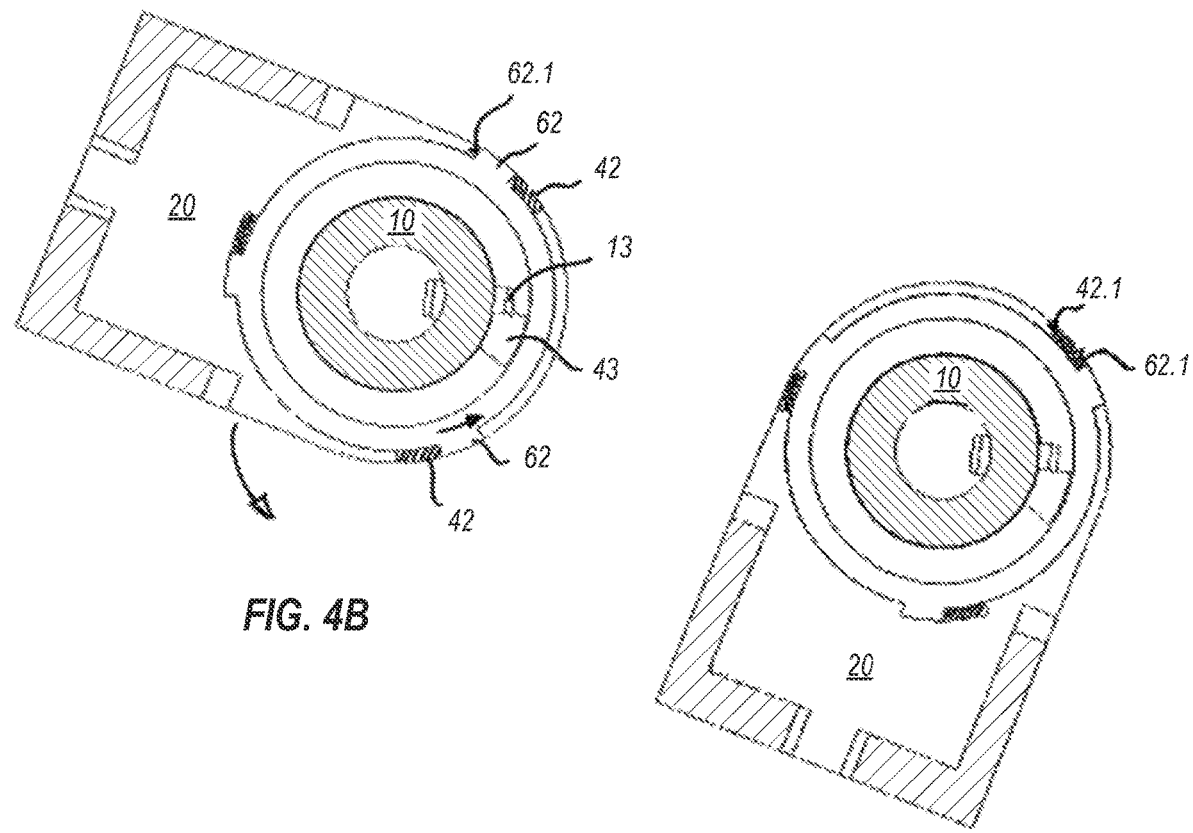
FIG. 4B
FIG. 4C

ROTATABLE CONNECTION WITH ROTATIONAL ANGLE LIMITATION

This is a divisional application from U.S. patent application Ser. No. 14/695,372, filed Apr. 24, 2015, the disclosure of which is incorporated herein by this reference.

The present invention relates to a rotatable connection of a stand apparatus to be arranged in an operating room which comprises an adaptable stop mechanism, which can be arranged between a spindle and a sleeve mounted rotatably around a rotational axis relative to the spindle and is configured to define at least two different relative rotational angles of the spindle relative to the sleeve or at least two different rotational ranges, the adaptable stop mechanism comprising: a first part, in particular in the form of an stop ring which can be mounted on the spindle such that it can be rotationally locked and comprises at least a first stop; and a second part which is provided non-rotatably on the sleeve; the first part being rotatably mounted relative to the second part. The present invention relates in particular to a rotatable connection with individual features as well as a carrier system or a stand apparatus with individual features of the appropriate further independent claim.

Stands, in particular ceiling stands such as, for example, ceiling supply units, monitor arms or so-called spring arms or central axes, usually have one or more carriers, which are height-adjustable or fixedly arranged in relation to a vertical position, by means of which a medical technology device fastened thereto can be moved and positioned, e.g. in an operating room, in particular also at an intensive care station. Frequently mounted on the stands are supply units with which medical-electrical end-devices can be supplied, for example, with media required during surgery. The carriers define an action radius of the medical technology device in which the medical technology device is positioned. The carrier can usually be rotated at least around a rotatable connection, in particular a rotational joint. The carrier can optionally be arranged as height-adjustable and/or swiveled up and down around an at least nearly horizontally oriented axis.

A rotational movement of individual parts, be it an absolute rotational movement or a rotational movement relative to another carrier, should be limited to a prescribed angle in many cases. This can prevent the carrier from being rotated by more than 360° in relation to another carrier and thereby twisting, crushing or even tearing the lines routed in the carrier. Rotational angle limitation can be provided, for example, in the form of a stop which a carrier strikes at a certain rotational angle, for example 300°. The stop can be fixedly mounted on the carrier, for example, particularly in the form of a locking pin introduced in the radial direction. The stop provides a predefined rotational angle. While such a rotational angle limitation can ensure that a maximum rotational angle is not exceeded, it usually also has the disadvantage that it limits the freedom of movement of the stand, i.e. no longer allows a supply unit, for example, of the stand to be arranged in the desired positions. The radius of action of the stand is limited, particularly without taking a particular spatial situation into consideration. It is therefore necessary to determine in each individual case by what stop position the rotational angle limitation can or should be defined. Properly determining rotational angle limitation, in particular the adequate positioning of the stop, can, however, be difficult even as early as the manufacturing of a particular stand, particularly if it has not been clarified where the stand is to be used. Rotational angle limitations that allow a rotational angle or rotational position to be subsequently adjusted are thus practical.

A device with an adjustable rotational angle is known from EP 2 325 541 B1. EP 2 325 541 B1 describes a two-part adaptable stop mechanism in which a ring-shaped part can be selectively positioned externally around a circumference of a first carrier or a joint of the first carrier, and the ring-shaped part comprises a plurality of recesses or projections arranged on the end face which allow it to be arranged at different rotational angle positions relative to the first carrier in a simple manner. Also arranged on the ring-shaped part is stop at which a second carrier can strike. The ring-shaped part allows a rotational angle of the two carriers relative to one another to be set. The stop mechanism is arranged within a collar of the second carrier. The ring-shaped part can be raised by inserting a tool into a groove running around an outer casing surface of the ring-shaped part to position the ring-shaped part at a desired rotational angle position relative to the first carrier. A further ring-shaped part is additionally provided on the first carrier and can be positioned relative to the ring-shaped part. The two ring-shaped parts are arranged within a collar and are radially and externally enclosed and covered by the collar. Arranged in the collar is a locking pin introduced in radial direction which engages in an intermediate space formed by the two ring-shaped parts. The extent of the intermediate space in the circumferential direction is defined by the relative rotational position of the first part relative to the second part. The angular range in which the two carriers can be rotated relative to one another can be defined over the extent of the intermediate space in the circumferential direction. The stop mechanism is essentially arranged on the first carrier and works together with the second carrier via the radially introduced locking pin.

DE 38 08 327 A1 describes a stop mechanism in which a threaded pin can be displaced in a threaded hole in radial direction to set different rotational angle positions.

The present invention seeks to solve the problem of furnishing a rotatable connection which allows a rotational angle or rotational (angle) range to be set in a simple manner. In particular, it also seeks to solve the problem of furnishing a stand apparatus with rotational angle limitation in which individual carriers of the stand apparatus can be positioned in an operating room in a flexible manner by means of an adjustable rotatable connection.

This problem is solved through a rotatable connection for a stand apparatus to be arranged in an operating room which comprises an adaptable stop mechanism which can be arranged between a first connection component (in particular a connection component of the rotatable connection) and a second connection component (in particular a connection component of the rotatable connection) mounted rotatably around a rotational axis relative to the first connection component and is configured to define at least two different relative rotational angles of the connection components relative to the one another or at least two different rotational ranges, the adaptable stop mechanism comprising:

a first part which can be mounted rotationally lockable on the first connection component and features at least one stop;

a second part, which can be provided or arranged non-rotatably on the second connection component;

the first part being rotatably mounted relative to the second part;

the adaptable stop mechanism comprising a stop device with at least one counter-stop which is arranged axially (i.e. in relation to the axial direction of the rotational axis) between the two parts and can thereby interact with the two parts, wherein the at least one counter-stop corresponds to the at least one stop, the stop device being configured to define the different relative rotational angles or rotational ranges by means of the at least one counter-stop. In this way, an adjustable, rotatable connection can be provided in a simple manner. Adjustment can be made by, for example, axially displacing and rotating the stop mechanism, particularly in a manual manner. The separate stop mechanism can be arranged between the two parts at different rotation positions. A pin or locking pin arranged in radial direction is not required. Rather, the components can be positioned toward one another in axial direction. The counter-stops can be secured to the stop mechanism in predefined positions. This also makes it possible to define different rotational ranges, thus, for example, a rotational range from true north (i.e., geographic north) of 360° in clockwise direction and counterclockwise direction, or a rotational range starting from east of 360° or a rotational area from true north of 360° In this manner, the action radius of, for example, a stand apparatus can also be adapted and set in relation to an arrangement near a wall or in a corner. The (absolute/maximum) magnitude of the rotational angle is preferably strictly prescribed, for example at 360°, 400° or 420°, through the geometric design of the stop mechanism, in particular the stop device. The starting point of the rotational movement is adjustable.

By arranging the stop mechanism both on the first connection component and on the second connection component, a stop device can be provided which can be arranged and repositioned between the two connection components in a simple manner, in particular through the axial displacement of the first part relative to the second part.

The number of components can be kept low by using a stop device having one or more counter-stops. The entire stop mechanism is preferably constructed from only three components, in particular the first part, the second part and the stop device.

The connecting of the first part to or mounting thereof on the connection component described as rotationally lockable arrangement can be furnished through, for example, two projections which strike one another or can engage one another, i.e. a form-fitting connection. The first part is rotatably arranged around the rotational axis, in particular together with the first connection component. When engaged, the first part can be rotated jointly with the first connection component, which can be ensured through a stop in the form of a pin or a locking pin. A rotationally locked arrangement can also include an arrangement which, while permitting a relative movement between the particular part and the particular connection component, is limited starting at a certain rotational angle by some type of stop. Once the part makes contact with the stop, a relative rotational movement between the part and the connection component is no longer possible in the corresponding rotational direction. In other words, a rotationally locked arrangement prevents the first part from being further rotated around the first connection component, at least in a rotational direction. A rotationally locked arrangement allows a rotational range, in particular with a rotational angle greater than 360°, to be set. A rotationally locked arrangement can also include a non-rotating arrangement, i.e. a groove-spring-connection.

The connection of the second part to or the mounting thereof on the connection component described as non-rotating arrangement can be realized, for example, through a groove-spring-connection, i.e. a connection which defines only a single relative position of the two components to one another. A non-rotatable arrangement, connection or mounting can also include an arrangement in which the second part (one-piece) is designed as an integral part of the connection component. In particular, the second part can be integrated in a second connection component realized as a sleeve.

While the first part is preferably mounted on the first connection component in a rotationally locked manner, this is preferred only in regard to a rotational movement. In other words, the rotationally locked arrangement does not necessarily involve a predefined axial position. Rather, the first part is mounted preferably on the second connection component in axial direction, in particular by means of the stop device and/or the second part. The first connection component can be axially positioned preferably on the second connection component in axial direction, or vice versa, by means of a Seeger ring, for example.

The term rotatable connection is preferably understood to mean an arrangement that ensures a rotation of components in relation to one another at a definable angle. A rotatable connection is, for example, a connection between a sleeve and a spindle, wherein the rotatable connection does not necessarily include the sleeve and spindle, but rather only the bearing or bearing surfaces provided thereon for these components, for example. The rotatable connection preferably comprises at least a swivel joint or forms a part of the swivel joint. A swivel joint is preferably understood to mean a joint which allows at least a rotation around one or more rotational axes, wherein a translatory degree of freedom can also be realized. The swivel joint is preferably arranged at the interface between two individual carriers, but can also subdivide an individual carrier into multiple sections. The swivel joint can be provided, for example, at the interface between a spindle and a sleeve.

A stand apparatus is preferably understood to mean an apparatus for holding, arranging in stationary position and/or displacing at least one medical technology device which can be fixedly mounted on a wall (on a wall bracket) or a ceiling or also on the floor of an operating room or any other room for medical purposes, i.e., a ceiling stand for example. The stand apparatus cannot be completely displaced freely in the operating room, but can be displaced only within a certain action radius, in particular relative to a fastening point or mounting point arranged on a ceiling or wall of the operating room. The stand apparatus can be designed as a ceiling supply unit mounted on a ceiling and comprising one or more supply consoles, mounted and positionable on one or two carrier arms. The stand apparatus can also be designed as a monitor carrier. The stand apparatus can also be designed as a so-called spring arm, particularly for mounting on a wall, and can feature a light, for example. The stand apparatus can also be designed as a so-called central axis, particularly for mounting on a ceiling, and can comprise a plurality of carrier systems having at least one carrier on which a monitor or light, for example, is mounted. The stand apparatus does not necessarily have to be fixedly mounted on a wall, but rather can also be mounted on a mobile substructure. The mobile substructure can be positioned in a stationary manner in the room by means of brakes, for example. An adaptable stop mechanism is expedient in this case as well.

An adaptable stop mechanism is preferably understood to mean any device which can limit a rotational angle and/or rotational range of a carrier, in particular relative to another carrier or relative to a (imaginary) rotational axis fixedly positioned in the room, for example a rotational axis running through a fixedly arranged fastening point on a wall of a room. The adaptable stop mechanism at least also comprises a form-fitting connection or is designed for a form-fitting connection. The adaptable stop mechanism can additionally also function in a force-locking manner.

Rotational range is preferably understood to mean an angular range in which a carrier can be rotated relative to another carrier or a wall. The angular range can be, for example, 330° or even more than 360°. The angular range can be constant, but defined, for example, in relation to different circumferential positions, i.e., from 0° to 300° relative to north or from 30° to 330° relative to north, for example. The rotational range can be defined by different rotational angle positions.

The first part is preferably understood to mean a part which is somehow coupled rotationally locked to the rotational movement of the first connection component (a spindle, for example) and interacts with the first connection component preferably in a form-fitting manner. The first part can preferably be displaced in axial direction relative to the first connection component. A relative displacement toward one another in circumferential direction is blocked or can be blocked starting at a certain rotational angle. The first part can be designed as ring-shaped, for example, and can thus be referred to as a stop ring which defines at least one stop. A stop is preferably understood to mean any projection or ledge, in particular also protruding in axial direction.

The second part is preferably understood to mean a part which is non-rotatably coupled to the rotational movement of the first connection component (a sleeve, for example) and, for example, interacts with the second connection component in a form-fitting manner, in particular in a rotationally synchronous manner. In other words, the second part is provided on the second connection component in such a manner that the second part and the second connection component realize the same rotational movement in each case. The position of the second part relative to the second connection component is then predefined and also unchangeable. The second part can be formed by the second connection component, e.g. integrally cast thereon. The second part is preferably stationary on the second connection component, thus also fixed axially, i.e. cannot be displaced in axial direction relative to the second connection component. The second part is preferably connected only to the second connection component or formed thereby and is decoupled from the first connection component and interacts indirectly with the first connection component only by means of the stop device and the first part. The second part can be designed as ring-shaped, for example, and can comprise at least one form-fitting contour in the form of toothing, e.g. a sawtooth contour, in particular on the interface with the stop device. The second part can thus be referred to as a toothed ring. Preferably no stops or counter-stops defining a rotational range are arranged on the second part. Stops of this type are not necessary, particularly because a relative rotational movement between the second part and the stop device must not or should not occur. The second part is preferably configured to mount the stop device in a rotatably fixed manner in an adjustable rotational position on the second connection part so that a stop of the first part can strike the stop device to transfer a correspondingly generated reaction force from the stop device to the second part. In other words, the first part is preferably connected to the second part only in an indirect manner, in particular via the stop device.

The stop device is preferably understood to mean a part which is configured for the purpose of furnishing a counter-stop in a stationary position relative to one of the connection components, in particular relative to the second connection component, wherein a (rotational) force exerted on the stop device in circumferential direction, thus a torque, can be transferred between the connection components via a counter-stop. The stop device is preferably configured to prevent direct interaction between the first and second part. The stop device is preferably interposed between the first and second part and configured to transfer a torque between the first part and the second part. The stop device preferably extends at least in sections around the rotational axis, the stop device preferably being designed as ring-shaped and running circumferentially around the rotational axis. In this case the stop device can be described as an adjusting ring, for example. Counter-stop is preferably understood to mean any protrusion, ledge or projection.

An arrangement "axially between" the first and second part is preferably understood to mean an arrangement in which the first and second part are not coupled directly to one another, but rather indirectly via the stop device. An arrangement "axially between" preferably means that the first part in axial direction does not have to engage the second part, but rather that an engagement or interaction between the first part and second part can be ensured (solely) by means of the stop device.

A rotational angle position is preferably understood to mean a relative rotational position of a carrier in relation to another adjacent carrier or in relation to an axis oriented fixedly in space in a defined direction. The rotational angle position can be described in relation to an absolute (horizontal) angle, e.g. around a (imaginary) vertical rotational axis.

The stop device is preferably configured to transmit a rotational force acting in circumferential direction and exerted on the stop or counter-stop between the first and second part, i.e. from the first part to the second part and/or from the second part to the first part. In other words, the stop device is configured to couple the two parts to one another, in particular also to define a certain rotational angle range of the parts relative to one another.

According to an exemplary embodiment, the stop device can be positioned on one of the two parts in at least two different rotational angle positions such that it is non-rotatable in relation to one of the two parts, in particular to the second part. In this way, a starting point or initial point of a particular rotational angle range can be set, in particular at a rotational angle greater than 360°. The counter-stop is preferably positioned on the stop device in a stationary manner. The counter-stop can be provided integrally on the stop device, i.e., the stop device and the counter-stop constitute a single part. The counter-stop or at least a counter-stop of a plurality of counter-stops can optionally also be secured to the stop device by means of a threaded connection in radial or axial direction. This simplifies the setting of a particular rotational angle, for example.

The first part is preferably arranged such that it can be displaced along the rotational axis in axial direction. In this way, the stop device can be shifted in axial direction together with the first part in a simple manner to adjust the rotational range or rotational angle. It is not necessary to remove any pin engaging in radial direction or a collar accommodating the pin to displace the two parts relative to one another in axial direction. In this example, the first part can be guided to an inner casing surface on the second connection component via a centering device.

The stop device is preferably arranged such that it can be displaced along the rotational axis in axial direction, in particular together with the first part. This allows the rotatable connection to be adjusted in a simple manner. For example, only the stop device needs to be engaged, and the first part can be shifted axially together with the stop device, in particular upward against the force of gravity.

The first part, the second part and the stop device are preferably arranged linearly in axial direction one-after-the-other. In this way the rotatable connection, in particular the starting or initial point of the rotational angle range, can be adjusted in a simple manner, in particular by means of the first part and the stop device being shifted away from one another axially.

Axially displacing the parts and the stop device toward one another allows the rotational range to be adjusted in a simple manner. A damping element can also be provided between the parts or between one of the parts and the stop device in a simple manner. The linear arrangement one-after-the-other also facilitates simple assembly. A linear arrangement one-after-the-other can be understood as an arrangement in which (disregarding a possibly interposed damping element) the first part comes contacts the stop device and in which the stop device contacts the second part.

The stop device is preferably arranged in axial direction between the two parts and overlaps in axial direction the second part in the area of a form-fitting contour and overlaps in axial direction the first part in the area of the stop. Having the first part and the stop device arranged overlapping one another in axial direction allows the stop mechanism to be furnished in the form of a connector system of simple construction. Good stability of the arrangement can be ensured, in particular because the first part and the stop device can be stabilized against tilting, specifically by means of the inner and or outer casing surface of the stop device. The first part is preferably dimensioned and geometrically designed such that the first part, in particular the at least one stop, can be arranged around the stop device at least partly outside and/or at least partly within the stop device. This arrangement makes it possible to arrange the at least one counter-stop on an outer or inner casing surface of the stop device, thereby allowing a force to be further conducted in circumferential direction. The counter-stop can be designed to be especially robust and solid.

The first and/or second part preferably extends at least in sections around the rotational axis, the first and/or second part preferably being designed as ring-shaped and running circumferentially around the rotational axis.

According to an embodiment, the first part is designed as ring-shaped and comprises two or more stops which are arranged opposite one another and protrude in axial direction from a disc, in particular on an outer casing surface or circular ring surface. The first part can comprise an area that is designed as rotationally symmetrical, in particular disc-like. A disc is preferably understood to be a primarily flat part extending essentially in a radially oriented plane, while extending to a clearly lesser degree in axial direction orthogonal to the plane. The advantage of the disc design is that a sliding surface can be furnished on a particular end face of the disc in a simple manner.

According to an exemplary embodiment, the first part and the stop device and optionally also the second part can be axially arranged or axially positioned or mounted on the second connection component in axial direction. Preferably at least the first part and the stop device are positioned axially on the second connection component in axial direction solely through the force of weight. This free arrangement (without additional fastening means) allows an adjustable or adaptable stop mechanism to be furnished in an especially simple manner.

According to an exemplary embodiment, the stop device is arranged such that a nonrotatable arrangement of the stop device on the second part is ensured (in particular exclusively) by weight as well as gravity acting on the stop device. In this case, adapting the stop mechanism requires only displacing the stop device, in particular jointly with the first part, against a weight force acting on the stop device. It is not necessary to remove any radially introduced locking pins or bolts. Instead, the first part can be axially secured by means of a circlip.

According to an exemplary embodiment, the second part has a form-fitting contour for setting the individual rotational angle positions, particularly on an inward pointing casing surface and/or on an end face pointing in axial direction. The stop device has a corresponding form-fitting contour, in particular on an end face pointing in axial direction to the second part or second connection component. In this way, an easily accessible plug-in connection can be furnished by means of which the stop mechanism can be adjusted or adapted.

A form-fitting contour is preferably understood to mean a toothing or toothed contour or a contour with regular interruptions or protrusions. The individual tooth can be shaped primarily as desired. The individual tooth is preferably of cuboid shape with a rectangular cross-section. The form-fitting contour is not necessarily exclusively form-fitting, but can also be force-locking. The form-fitting contour is preferably not materially bonded to ensure that the at least one counter-stop can be reversibly positioned at various rotational angle positions as frequently as desired.

The form-fitting contour of the second part is accessible in an axial direction at least nearly parallel to the rotational axis such that the stop device with the corresponding form-fitting contour in axial direction can be inserted onto the second part. This simplifies both assembly and adjustment.

The form-fitting contour of the second part and the form-fitting contour of the stop device are each designed as a toothed ring, the teeth of which preferably project in an axial direction nearly parallel to the rotational axis. Toothed ring is preferably understood to mean a contour designed to be rotationally symmetrical in relation to the rotational axis with a plurality of individual teeth, the teeth being arranged at a uniform distance from one another. The embodiment as toothed ring offers, for example, the advantage of smaller adjustment intervals, since the more teeth that are provided, the more precisely the starting or initial point of the rotational angle range can be defined, e.g., in 10°-increments.

According to an exemplary embodiment, the first part and the stop device together form a bearing, in particular a slide bearing, with the first part lying on the stop device. In this way, the first part can be displaced relative to the stop device or the second part with low friction even if a normal force acts on the contact surface between the first part and the stop device. The normal force does not have to be large, because it can correspond to the weight force of the first part, for example. The bearing can facilitate a free-moving rotatable connection and optimize the interaction of the individual components of the rotatable connection. The stop device is preferably arranged between the first part and the second part such that the first part contacts only the stop device, but not the second part. The second part likewise contacts only the stop device. In other words, the first part interacts with the second part (preferably only) through the stop device.

According to an exemplary embodiment, the first part comprises a sliding surface arranged on an end face, particularly on an end face pointing toward the stop device, and is configured to rotate with the sliding surface on the stop device in a sliding manner. Additionally, the stop device can comprise a sliding surface arranged on an end face, in particular on an end face pointing toward the first part and away from the second connection component, and is configured to mount the first part by means of the sliding surface for a sliding rotational movement around the rotational axis. The sliding surface of the first part and/or the sliding surface of the stop device can preferably be designed, for example, as either a fully continuous or also segmental annular circular ring surface. In this way, the bearing for the second part can be furnished in a simple and cost-effective manner. The planar resting on the stop device allows a robust stop mechanism to be furnished which can be manually operated in a simple manner. No bolts or other securing means or fastening elements have to be loosened. At the most there would be an optionally provided circlip for axially securing the first part. The interlocking of the components, i.e., the first part, the stop ring and the second part can be ensured through the force of gravity alone.

The planar mounting on the ring-shaped end faces can ensure exact positioning of the components relative to one another and render the rotatable connection very robust and allow it to move very smoothly.

A sliding surface is preferably understood to mean a surface which has a low frictional coefficient for sliding friction, be it due to an especially low roughness or an especially smooth surface, be it due to low-friction material with lubricating properties. The material for the stop device or adjusting ring can be, for example, coated or uncoated die-cast zinc.

The stop device is preferably designed as an adjusting ring with a form-fitting contour projecting from an end face in axial direction toward the second part. An adjusting ring is preferably understood to mean (disregarding any stops) a rotationally symmetrical part which can be positioned in various rotational angle positions, e.g. each offset by 15°, thus for example in 24 different rotational angle positions.

The stop device is a one-piece part that can be inserted onto the second part in axial direction and on which the at least one counter-stop projects preferably in radial direction, in particular from an outer or inner casing surface of the stop device. In this way, the space required in the axial direction (the required installation height) can be kept low and a flat construction can be realized.

According to an exemplary embodiment, the adaptable stop mechanism is configured to adjust a rotational area with a relative rotational angle greater than 360°, in particular between 360° and 420°. The rotational angle greater than 360° can be ensured in particular by arranging the first part on the first connection component not in a non-rotatable or torque-proof manner, but rather only in a rotationally locked manner. The first part preferably has a form-fitting element where an anti-rotation means, e.g. a pin, of the first connection element can make contact. The form-fitting element (in contrast to the stop of the first part) is preferably decoupled from the stop device, and thus does not interact with the stop device, at least not in terms of a coupled rotational movement. In this case, the starting or initial point for the rotational movement or the rotational angle range can be defined by means of the stop device, in particular by defining the relative position of the stop device relative to the second part. The proportionally large rotational angle of more than 360°, in particular up to 420°, offers the advantage of great flexibility, for example. The stops can be positioned without adversely decreasing the freedom of movement of the stand apparatus. In contrast, known rotatable connections usually allow only a rotational (angle) range to be set with a smaller rotational angle of maximally around 330°. In other cases, adjusting the rotational angle range is very laborious or is not possible at all.

According to an exemplary embodiment, the adaptable stop mechanism comprises a damping element, in particular made of elastomer, which corresponds to the second part and/or the stop device, in particular a form-fitting contour of the stop device projecting from an end face in axial direction. In this way it can be ensured that an impact is dampened when the stops come into contact with one another, thereby allowing the service life of the rotatable connection to be increased and/or the stand apparatus, in particular a medical technology device, to be protected. The damping element can prevent the carrier from swinging back or recoiling if the stops abruptly strike one another. A damping element is preferably understood to mean a rubber element having a geometry adapted to the particular form-fitting contour. The damping element can be in the shape of a meander, for example. The damping element can be arranged as inlay or jacket on the second part or on the stop device, namely on a particular form-fitting contour.

According to an exemplary embodiment, the rotatable connection comprises an intermediate element which is arranged, when viewed in axial direction, between the first part, in particular between the stop device, and the second connection component and at least one form-fitting contour for torque-proof connection with the stop device or the second connection component, wherein a form-fitting contour is arranged preferably on each of the two opposite lying end faces of the intermediate element. In this way, the stop mechanism arranged on the two connection components can be designed even more flexibly and can be provided in a simple manner in particular if cast sleeves are used. The form-fitting contour can ensure the non-rotation of additional elements, e.g. a slip ring inner part. The intermediate element offers advantages also in terms of manufacturing considerations. In particular, the form-fitting contour can be made on the second part in a simpler manner, specifically on a ring-shaped segment of a forked sleeve. For example, the use of an expensive die casting tool is not necessary.

An intermediate element is preferably understood to mean an element that can be nonrotatably coupled in a form-fitting manner to both the stop device and the second part. The intermediate element is an optionally provided, additional part on which a form-fitting contour can be realized in an especially simple manner, preferably on an end face. The intermediate element can also be provided for manufacturing reasons, for example. The intermediate element can be machined, in particular provided with the form-fitting contour(s), in a simple manner. The intermediate element can be handled in a simple manner and has easily accessible upper surfaces. The (particular) form-fitting contour is preferably made of grooves running in radial direction. The grooves can extend along the entire intermediate element. The grooves can optionally be provided in combination with springs in sections (as short grooves).

According to an embodiment, the intermediate element can be designed as a disc, in particular a ring-shaped disc. In this way, the intermediate element can be arranged in a row with the other components around the first connection component. The flat construction as a disc can also ensure that minimal space is required in axial direction.

According to an exemplary embodiment, the intermediate element is designed as wedge-shaped with a non-uniform axial dimension or thickness in relation to the axial direction.

In this way, the rotatable connection can be used in a simple manner with a cast sleeve on which a draft angle is provided. The wedge-shaped design allows the draft angle to be compensated so that the two parts and the stop device can be arranged oriented axially in relation to one another. In other words, the wedge-shaped geometry is arranged to compensate the draft angle of the sleeve.

The problem specified earlier is also solved by a carrier system for a stand apparatus for arranging in an operating room and for positioning a medical technology device in the operating room which comprises a rotatable connection according to the invention as well as the first connection component, in particular in the form of a spindle, and the second connection component, in particular in the form of a sleeve.

A carrier system is preferably understood to mean those components of the stand apparatus which at least partly also assume the function of holding and positioning the medical technology device. The carrier system can comprise a plurality of preferably rigid arms or carriers each displaceable relative to one another as well as a plurality of levers, joints or bearings.

A medical technology device is preferably understood to mean a light, a monitor and/or a supply console through which means for treating a patient and/or instruments for a surgeon and/or light, fresh air or other media required in the operating room can be furnished. The medical technology device preferably comprises some type of operating panel and/or some type of display device for graphically presenting patient data, for example.

According to an exemplary embodiment, the second connection component is designed as a sleeve, in particular a forked sleeve, wherein at least the stop device and the second part and preferably also the first part are arranged in the sleeve, in particular between two ring-shaped segments of the sleeve, preferably in one of the two ring-shaped segments, wherein the rotatable connection preferably comprises an intermediate element which is inserted into the sleeve, in particular into one of the two ring-shaped segments.

In this way a rotatable connection can be furnished, the stop device of which is easily accessible, thereby making it easier to adjust rotational angle or rotational angle range. The individual components can be placed in the sleeve in a simple manner, in particular from the side in radial direction. An additional intermediate element can also be placed in the sleeve, in particular in one of the two ring-shaped segments, in particular to compensate a draft angle and/or allow the form-fitting contours to be produced in a simple or cost-effective manner. The individual components can also be displaced relative to one another in axial direction in a simple manner to adjust rotational angle or rotational range.

The intermediate element also allows an especially flat construction of the rotatable connection in axial direction to be ensured, which is advantageous in the case of central axes, for example, most of which are already considerably expansive in axial direction.

The problem specified earlier is also solved by a stand apparatus for arranging in an operating room and for positioning a medical technology device in the operating room which comprises a rotatable connection according to the invention or the previously described carrier system having the rotatable connection according to the invention.

In a specific embodiment, the stand apparatus for arranging in an operating room and positioning a medical technology device in the operating room comprises a carrier system having at least one carrier, in particular a carrying arm, with a sleeve which is mounted rotatably (relative to a stationary part of the stand apparatus or to another carrier of the stand apparatus) around a rotational axis on a spindle on a rotatable connection, in particular a rotatable connection according to the invention, the rotatable connection comprising an adaptable stop mechanism which is arranged between the spindle and the sleeve mounted rotatably around the rotational axis relative to the spindle and is configured to define at least two different relative rotational angles of the spindle relative to the sleeve or at least two different rotational ranges, the adaptable stop mechanism comprising a first part, in particular a stop ring, which can be mounted rotationally locked on the spindle and features at least one ring;

a second part which is non-rotatably connected to the sleeve;

the first part being rotatably mounted relative to the second part; the adaptable stop mechanism comprising an adjusting ring arranged axially displaceable in the direction of the rotational axis and having at least one counter-stop which, when viewed in axial direction, is arranged between the two parts (and interacts with the two parts), wherein the at least one counter-stop corresponds to the at least one stop and wherein the adjusting ring is configured to define by means of the at least one counter-stop the different relative rotational angles or rotational ranges, and wherein the first part overlaps the adjusting ring in axial direction and is arranged radially inside and outside in relation to the adjusting ring and/or wherein, when viewed in axial direction, an intermediate element is arranged between the adjusting ring and the second part such that it is non-rotatable in relation to the adjusting ring and the second part.

In this way, the stand apparatus, in particular individual carriers, can be positioned relative to one another in a flexible manner. The counter-stop can be displaced in the second part to define a suitable rotational angle position, particularly in terms of a specific arrangement of the stand apparatus relative to other components in the operating room.

A carrier is preferably understood to be a boom or supporting arm which extends in a certain direction and can ensure the desired action radius for the various desired positions of the medical technology device particularly through a rotational movement around a rotatable connection. The carrier can optionally be pivoted up and down and/or displaced up and down in translatory motion. The carrier can also be a telescopic device with a (additional) degree of freedom of movement in the translatory direction along the longitudinal axis of the carrier. The carrier can be formed at least partly, for example, by a continuously cast section, in particular a continuously cast aluminum section.

The stop device makes it possible to define a rotational range or a specific rotational angle of the rotatable connection, in particular a reliable relative rotational angle of the two connection components in relation to one another.

The second part is preferably arranged on the carrier or, as the case may be, one of the carriers in the area of the rotatable connection. A contour or a stop can be fixed on one of the carriers in a stationary manner, by means of which the carrier can be positioned in the various rotational angle positions in relation to the other carrier or in relation to any other part arranged in a stationary manner.

Figure 2:
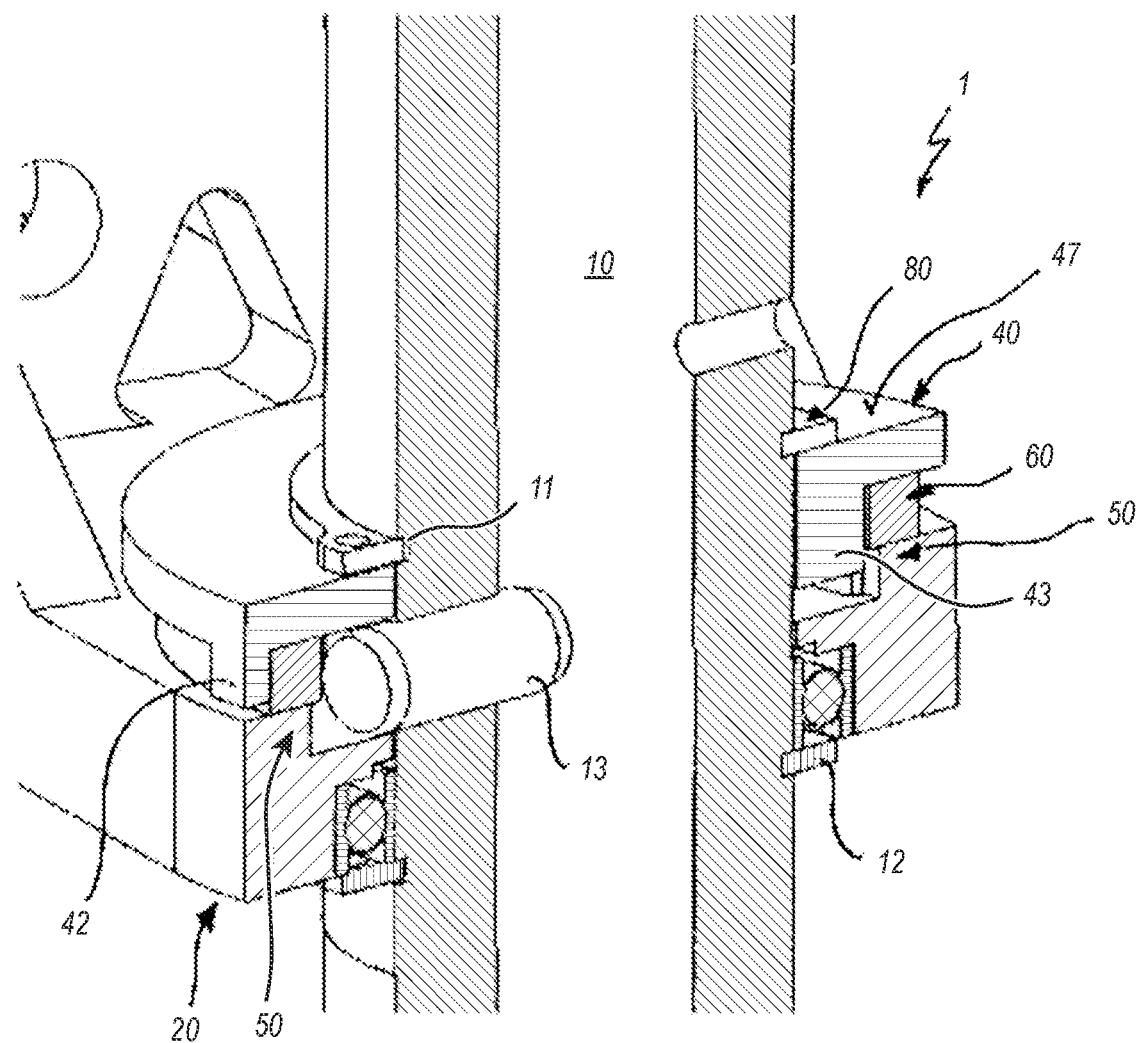
Figure 3A:
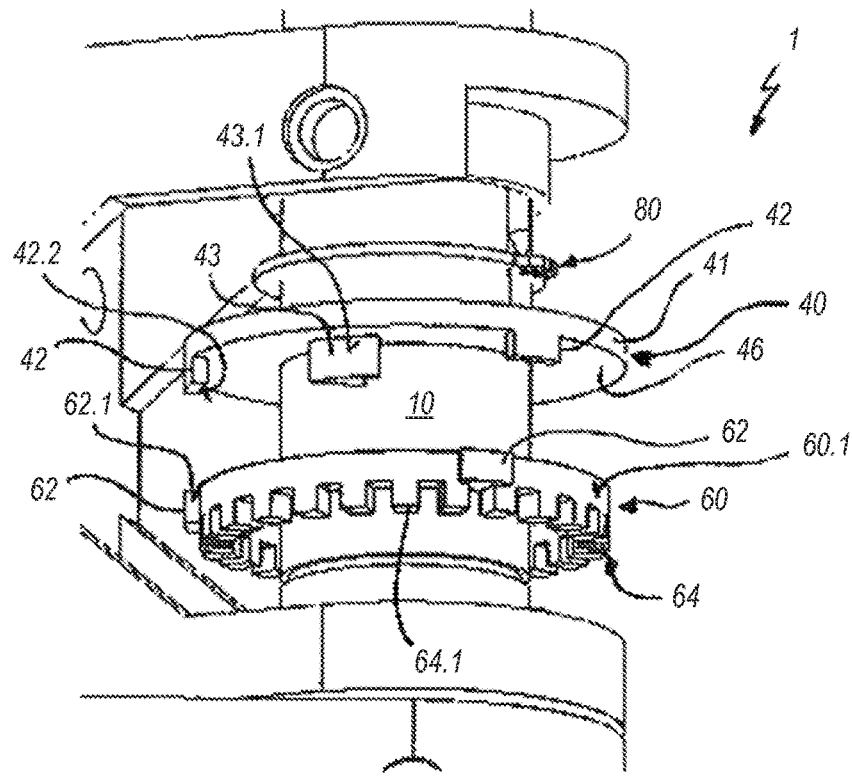
Figure 3B:
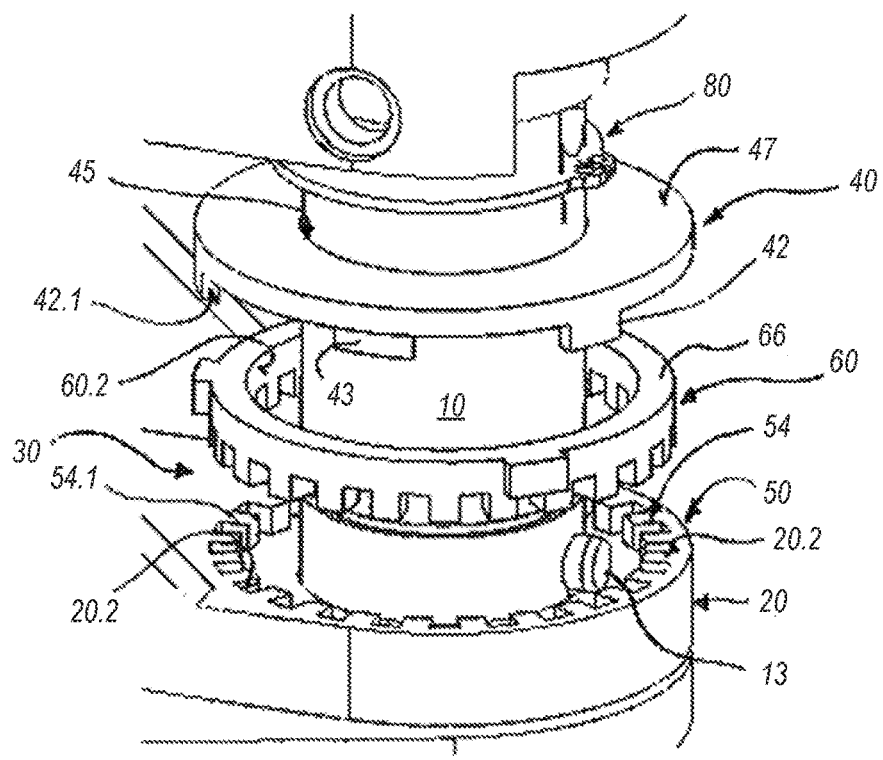
Figure 5:
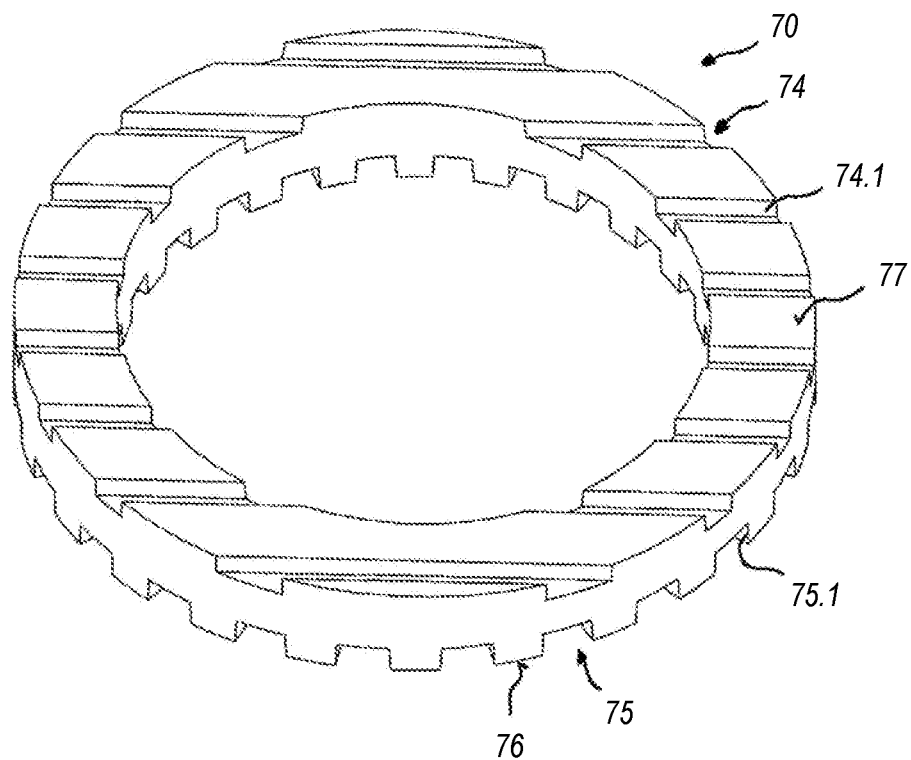
Figure 6:
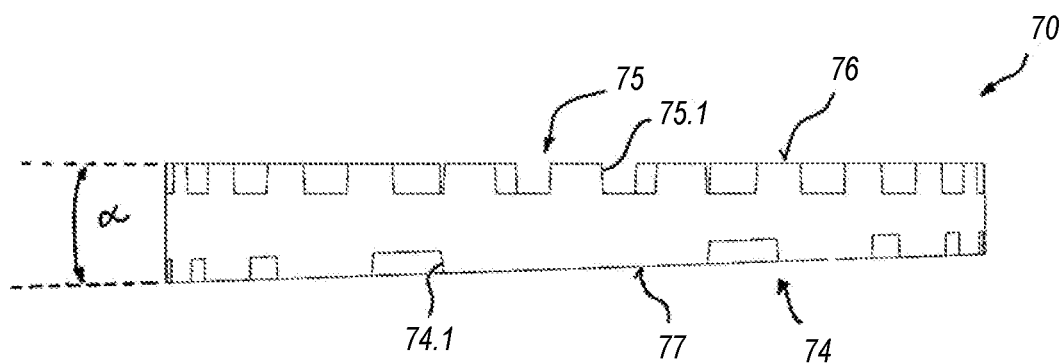

The invention is described in greater detail using exemplary embodiments illustrated in the following figures. Shown are:

FIG. 1 a schematic illustration in perspective view of a rotatable connection according to an exemplary embodiment of the invention;

FIG. 2 a perspective sectional view of the rotatable connection according to the exemplary embodiment shown in FIG. 1;

FIG. 3A a perspective side view of the rotatable connection according to the exemplary embodiment shown in FIG. 1 in exploded view;

FIG. 3B a perspective side view of the rotatable connection according to the exemplary embodiment shown in FIG. 1 in another exploded view;

FIGS. 4A, 4B and 4C a partly sectional top view of the rotatable connection according to the exemplary embodiment shown in FIG. 1 in various rotational angle positions;

FIG. 5 a perspective side view of an intermediate element of a rotatable connection according to a further exemplary embodiment of the invention;

FIG. 6 a side view of the intermediate element shown in FIG. 5; and

Figure 7:
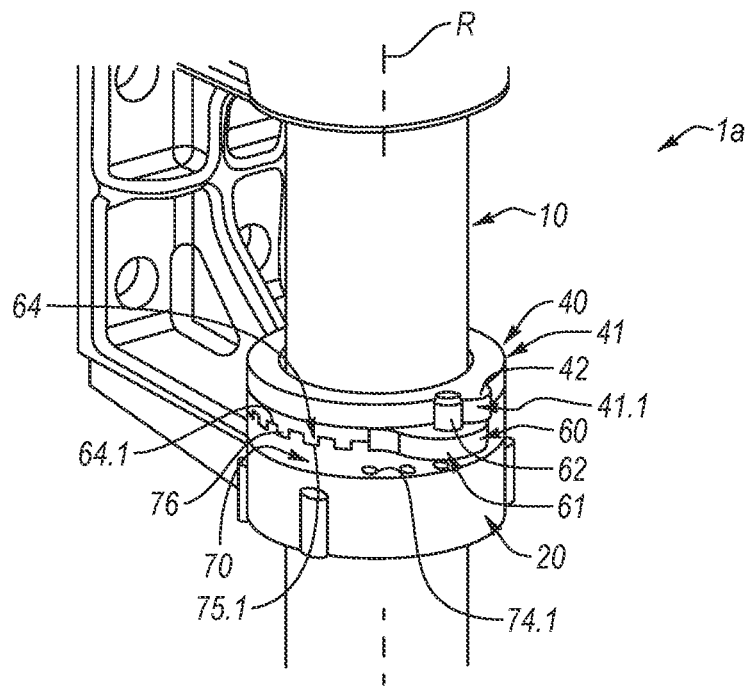
Figure 8:
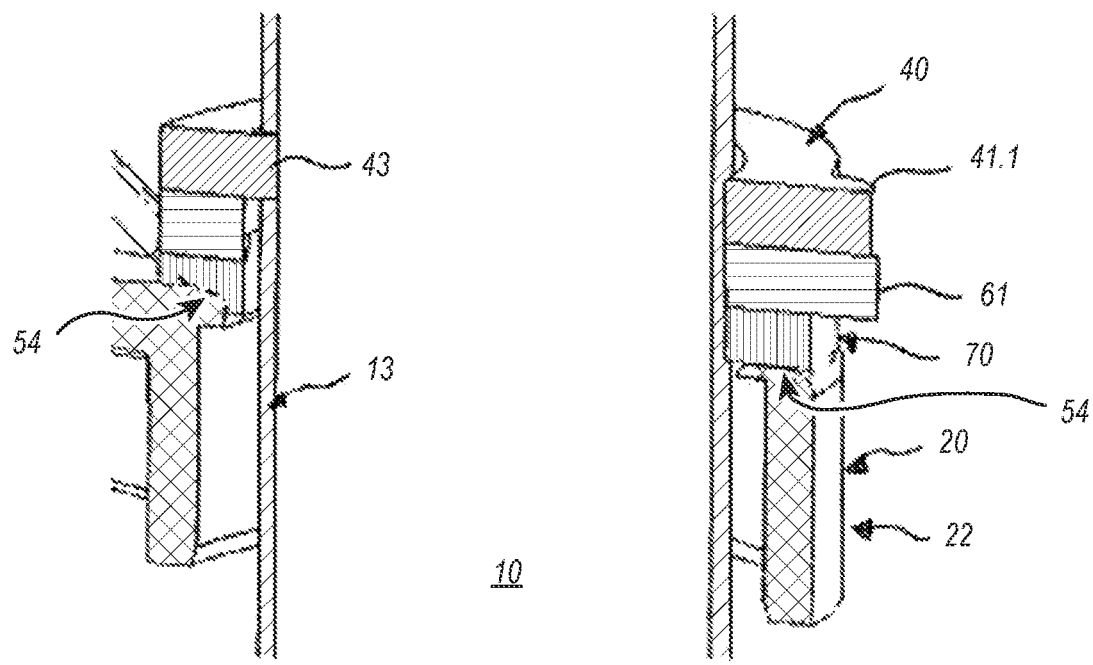
Figure 9:
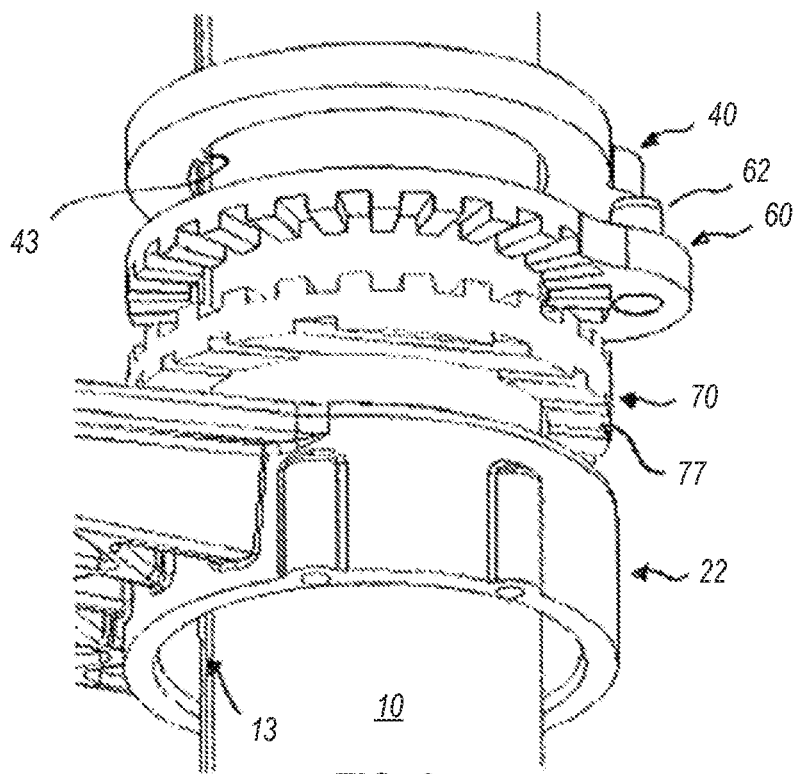
Figure 10:
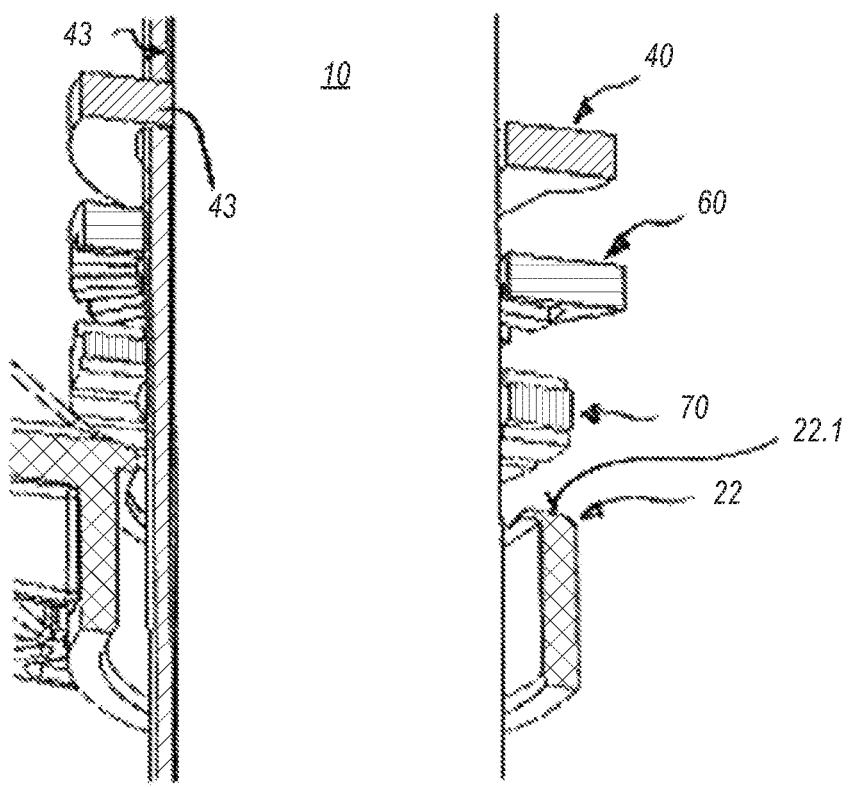
Figure 11:
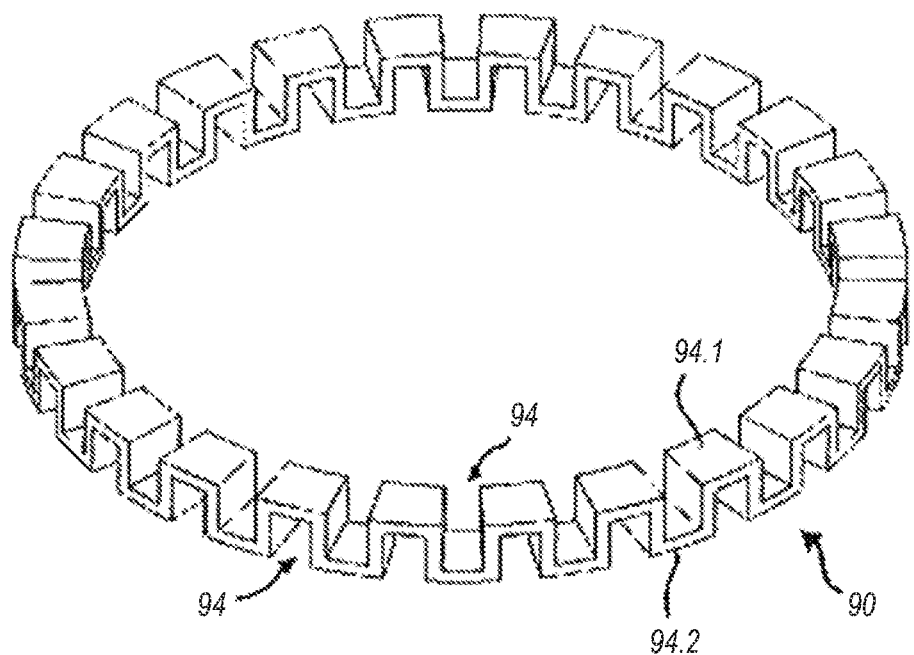
Figure 12:
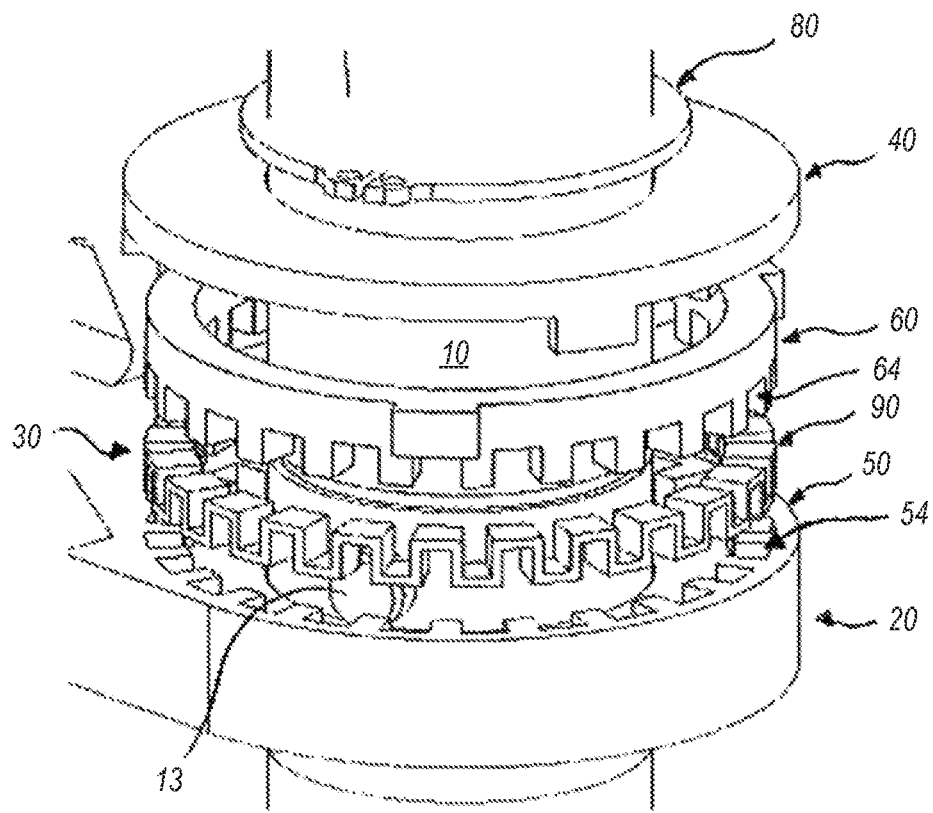

FIG. 7 a schematic illustration in perspective view of a rotatable connection according to a further exemplary embodiment of the invention;

FIG. 8 a perspective sectional view of the rotatable connection according to the exemplary embodiment shown in FIG. 7;

FIG. 9 a perspective side view of the rotatable connection according to the exemplary embodiment shown in FIG. 7 in exploded view;

FIG. 10 a perspective sectional view of the rotatable connection according to the exemplary embodiment shown in FIG. 7 in exploded view;

FIG. 11 a perspective side view of a damping element for a rotatable connection according to an exemplary embodiment of the invention; and FIG. 12 a perspective side view of a rotatable connection according to a further exemplary embodiment of the invention in exploded view.

In the description of the following figures, individual reference numbers apply to the additional figures unless it is explicitly stated that they relate to a particular figure.

FIG. 1 shows a rotatable connection which is arranged on a stand apparatus 100 around a rotational axis R. The stand apparatus comprises a carrier system with a first carrier 102 and at least one additional carrier (not explicitly illustrated). The rotatable connection 1 comprises a first connection component 10, particularly in the form of a spindle, and a second connection component 20, in particular in the form of a sleeve. The first carrier 102 is mounted around the first connection component 10 and is connected to the second connection component 20. The sleeve 20 can be described as forked and comprises two openings 21 each arranged in a ring-shaped segment 22 of the sleeve 20 through which the first connection component 10 is fed. Formed between the ring-shaped segments 22 is a cavity which is manually accessible in radial direction, particularly for adapting a stop mechanism 30. The axial position of the sleeve 20 on the spindle 10 can be defined by means of a Seeger ring or a lock nut secured to the spindle.

The rotatable connection 1 comprises an adaptable stop mechanism 30 arranged between the spindle 10 and the sleeve 20. The stop mechanism 30 comprises a first part 40 and a second part 50. In the exemplary embodiment shown, the first part 40 is designed as a stop ring and the second part 50 as a toothed ring (see FIG. 3B). The toothed ring 50 is arranged within the sleeve 20, in particular on an inner casing surface of one of two ring-shaped segments of the forked sleeve 20. The stop ring 40 comprises multiple stops 42 which protrude on an end face of the stop ring 40 in axial direction. The stops 42 are fixedly positioned on the stop ring 40. Arranged between the stop ring 40 and the toothed ring 50 is a stop device 60 which forms a part of the adaptable stop mechanism 30. In the exemplary embodiment shown, the stop mechanism 60 is designed as an adjusting ring. The adjusting ring 60 comprises multiple counter-stops 62 which are arranged on an outer casing surface of the adjusting ring 60 and protrude in radial direction. The counter-stops 62 are fixedly positioned on the stop ring 60. The stops 42 and the counter-stops 62 each feature at least one flat side surface 42.1, 62.1 (see FIGS. 3, 4) which preferably extend at least roughly in a plane running parallel to the rotational axis R. The flat side surfaces 42.1, 62.1 form stop surfaces at which the stops 42, 62 can come to a rest against one another when the stop ring 40 is rotated relative to the adjusting ring 60. The flat side surfaces 42.1, 62.1 correspond to one another. The adjusting ring 60 can be positioned nonrotatably on the sleeve relative to the sleeve in various rotational angle positions, as is described more clearly using the FIGS. 3A and 3B.

FIG. 2 shows how the stop ring 40 can be mounted rotationally locked on the spindle 10. The spindle 10 is designed as a hollow shaft at least in sections. Arranged in the spindle 10 is anti-rotation means 13, in particular a pin, which can ensure that the stop ring 40 can be rotated relative to the spindle 10 only within a certain rotational (angle) range. The stop ring 40 comprises a form-fitting element 43 which corresponds to the pin 13 and is arranged on the inner side of the stop ring 40. Owing to, for example, the dimension of the stop and counter-stop in circumferential direction, the rotationally locked arrangement allows a dead angle to be bypassed. The rotationally locked arrangement allows a predefined rotational range with a rotational angle greater than 330°, or also greater than 360°, in particular up to 420°. A rotationally locked stop ring 40 can also be called an intermediate ring, which bypasses a dead angle and is operatively arranged between the spindle 10 and the counter-stops 62.

The spindle 10 features a groove 11 for accommodating a circlip 80. The circlip 80 can prevent the stop ring 40 from becoming displaced upward in axial direction. The stop ring 40 comprises a (second) end face 47 which can contact the circlip 80. The circlip 80 can be removed in a simple manner to adjust the rotatable connection 1. For this purpose, the stop ring 40 can be shifted upward. The adjusting ring 60 is then shifted upward until the adjusting ring 60 no longer engages in the sleeve 20 or the (not illustrated in detail, realized on the inside of the sleeve 20) toothed ring 50. Next, the adjusting ring 60 is rotated and shifted downward again in a different rotational angle position and engaged with the sleeve 20 or the toothed ring 50. However, the circlip 80 is not necessarily required. The adaptable stop mechanism can be adapted even without any type of lock screws or circlips whatsoever.

The adjusting ring 60 has a diameter which is smaller than a divided circle on which the stops 42 are arranged and larger than a divided circle on which the form-fitting element 43 is arranged. In other words, the stop ring 40 surrounds the adjusting ring 60 in radial direction with the form-fitting element 43 lying inside relative to the adjusting ring 40 and the stops 42 lying outside relative to the adjusting ring 60. The inner diameter of an inner casing surface of the adjusting ring 60 is clearly larger than the outer diameter of an outer casing surface of the spindle 10. The adjusting ring 60 is not mounted on the spindle 10.

Rather, the adjusting ring 60 can be centered from outside on its outer casing surface on the second part 50 or in the sleeve 20. The stop ring 40 can be centered over the outer casing surface of the adjusting ring 60 via the stops 42. It is not necessary to center on the spindle 10. This can ensure a relative rotational movement with low friction.

FIG. 3A shows the rotatable connection 1 in an arrangement in which the rotational angle position can be adjusted. The adjusting ring 60 has been displaced upward in axial direction after the circlip has been 80 removed or released from the corresponding groove. In this way, a form-fitting contour 64 of the adjusting ring 60 can be detached from a corresponding form-fitting contour 54 of the toothed ring 50 shown in FIG. 3B or pulled out in axial direction. The adjusting ring 60 is arranged displaceably in axial direction along the rotational axis R, in particular together with the stop ring 40. The adjusting ring 60 and the stop ring 40 are arranged in axial direction one-after-the-other in a row and engage one another in axial direction. The form-fitting contour 64 is designed as toothing which projects in axial direction. The form-fitting contour 64 comprises a plurality of individual teeth 64.1 arranged in circumferential direction on the underside of the adjusting ring 60 at a uniform distance on a divided circle. The form-fitting contour 64 allows the adjusting ring 60 to be positioned in at least two different rotational angle positions non-rotatably in relation to the (not shown) second part or toothed ring.

A damping element (not visible here, shown only in FIGS. 11 and 12) can be arranged on the form-fitting contour 64, the damping element being able to act between the formfitting contour 64 and the form-fitting contour 54 of the second part 50 shown in FIG. 3B. The damping element can be designed, for example, as a meander-shaped ring made of an elastomer, with a geometry corresponding to that of the teeth 64.1.

FIG. 3A shows that the adjusting ring 60 has three counter-stops 62 (two of which are visible) which are arranged displaced from one another by an angle of approximately 120° in circumferential direction. Likewise arranged on the stop ring 40 are three stops 42 which are arranged displaced from one another by an angle of approximately 120° in circumferential direction. Additionally, the form-fitting element 43 is arranged at a circumferential position at least roughly centered between two of the three stops 42. This arrangement of the stops 42 and the form-fitting element 43 relative to one another can, in particular, also ensure a favorable distribution of load.

FIG. 3A additionally shows a disc-shaped section 41 of the stop ring 40. The three stops 42 project from the disc-shaped section 41 in axial direction. The stops each have a concave or concavely curved inward inner surface 42.2 by means of which they can come to a rest at an outer casing surface 60.1 (with at least approximately the same curvature radius) of the adjusting ring 60. The form-fitting element 43 has a convex or convexly curved outward outer surface 43.1 by means of which the form-fitting element 43 can come to a rest at an inner casing surface 60.2 (with at least approximately the same curvature radius) of the adjusting ring 60. In this way, a relative rotational movement can be realized without jamming and by means of abutting in a sliding manner and mutual guiding or centering.

FIG. 3B shows how the adjusting ring 60 can be coupled to the sleeve 20. The formfitting contour 54 is arranged at an inwardly pointing casing surface 20.2 of the sleeve 20 and projects inwardly in radial direction. The form-fitting contour 54 comprises a plurality of individual teeth 54.1 arranged in circumferential direction on the casing surface 20.2 at a uniform distance on a divided circle. The adjusting ring 60 can be arranged radially between the spindle 10 and the sleeve 20 in a cavity, and the anti-rotation means or the pin 13 protrudes into a cavity formed radially between the spindle 10 and the adjusting ring 60 in which the form-fitting element 43 can be displaceably arranged. The adjusting ring 60 can be arranged in radial direction between the form-fitting element 43 and the stops 42.

FIGS. 3 and 4 show that the stop ring 40 can, via a (first) end face 46 come to rest on a corresponding end face 66 of the adjusting ring 60 and glide along it when a relative rotational movement occurs. The end face 46 features a ring-shaped sliding surface section (or a bearing) which is arranged between the stops 42 and the form-fitting element 43. In other words, the adjusting ring 60 forms a bearing for the stop ring 40, in particular a sliding surface. For this purpose, the end face 66 can also have, for example, a coating with a low frictional coefficient or the adjusting ring 60 can be made at least partly from an appropriate material. The same applies for the stop ring 40 as well as the surfaces 42.2 and 43.1 and 46. However, the force acting on the end face 66 is not large, with the stop ring 40 being only of comparatively low weight. A frictional force between the stop ring 40 and the adjusting ring 60 can be nearly negligible in this arrangement. The end faces 46, 66 as well as appropriate sections can also be referred to as sliding surfaces and sliding surface sections, respectively.

The mode of function of the stop mechanism is briefly described below on the basis of FIGS. 4A, 4B and 4C: the spindle 10 (and with it also the radial pin 13 secured in the spindle 10) forms a fixed component, while the sleeve 20 constitutes the movable component. When a carrier (not shown) is displaced, the sleeve 20 is rotated counterclockwise relative to the spindle 10 starting from a relative position shown in FIG. 4A until the form-fitting element 43 of the stop ring (of which only the shaded stops 42 and the formfitting element 43 are visible in the sectional view shown) encounters the radial pin 13, corresponding to a rotational angle of approximately 330° in this case. The adjusting ring 60 is arranged non-rotatably on the sleeve 20 and rotates to the same extent as the sleeve 20. Starting from the rotational point shown in FIG. 4B, a relative movement between the stop ring and the adjusting ring 60 is possible. In particular, the adjusting ring 60 can slide beneath the stop ring relative to the stop ring and can be further rotated until the corresponding counter-stop 62 strikes the side surface 62.1 at the corresponding side surface of the stop 42 of the stop ring, which in this exemplary embodiment allows a relative rotation of an additional 90°. The side surface of the stop 42 labelled 42.1 in FIG. 4C is then exposed, and the corresponding counter-stop 62 is brought with its side surface 62 facing forward in rotational direction to a rest at the opposite side surface of the stop 42. In the position shown in FIG. 4C, the sleeve 20 was rotated counterclockwise around the spindle 10 by more than one complete revolution. This rotationally lockable coupling between spindle 10 and adjusting ring 60 can ensure a rotational range greater than 360°, e.g. up to 420°. The mechanism can accordingly be used in the opposite rotational direction.

FIG. 3B also indicates a centering means 45 of the stop ring 40 by means of which the stop ring 40 can be centered in relation to the spindle 10. The centering means 45 can be formed by an inner casing surface or a section of an inner casing surface of the stop ring 40. The inner casing surface does not necessarily have the same diameter as the outer casing surface of the spindle 10, but rather can also be of somewhat greater diameter to facilitate a simple relative shifting with little friction, be it in circumferential or axial direction. The centering device 45 can additionally be formed also by an inwardly pointing surface section of the form-fitting element 43, thereby ensuring even more effectively that no jamming occurs on the spindle 10 when the stop ring 40 is displaced axially. However, the centering device 45 does not have to solely ensure the arrangement of the stop ring 40. Instead, it can be provided optionally (additionally). Centering can be also be realized simply through the concave inner surface 42.2 of the stop ring on the adjusting ring 60, with it being possible to center the adjusting ring 60 itself on the second part. These centering options permit a simple arrangement of components that can be arranged relative to one another in a precise manner.

In the exemplary embodiment shown, a particular rotational range with a rotational angle greater than 360°, in particular a rotational angle between 360° and 420°, can be achieved FIG. 5 shows an intermediate element 70 which has at one end face (as shown on the top side) a first form-fitting contour 74 and at another end face (as shown on the bottom side) a second form-fitting contour 75. The form-fitting contours 74, 75 each have individual grooves 74.1, 75.1. The grooves 75.1 arranged on a first end face 76 extend in radial direction. The grooves 75.1 are preferably arranged at a uniform angle to one another, i.e., at a uniform distance from one another when viewed in circumferential direction. The grooves 74.1 arranged on the second end face 77 extend in a straight line and are preferably oriented parallel to one another. The grooves 74.1 are preferably spaced at a uniform distance from one another. The intermediate element 70 is of ring-shaped design, and the end faces 76, 77 are flat or planar. The intermediate element is designed as a ring-shaped disc.

The intermediate element is shown in side view in FIG. 6. As FIG. 6 illustrates, the first end face 76 is arranged at an angle α in relation to the second end face 77, corresponding to the slope of a draft angle. The angle α is preferably around 1.5°. The end faces 76, 77 are not parallel. The intermediate element 70 is designed as wedge-shaped, in particular as a wedge-shaped annular disc. In this way, a draft angle of the sleeve can be compensated as is described in greater detail aided by FIG. 7. The end face 76 preferably corresponds to the end face which is coupled to the adjusting ring 60.

FIG. 7 shows an exemplary embodiment differing from that shown in FIGS. 1 through 3B in that the intermediate element 70 shown in FIGS. 5 and 6 is provided. Viewed in axial direction, the intermediate element 70 is arranged between the sleeve 20 and the adjusting ring 60. The intermediate element 70 is placed in the sleeve 20. As FIG. 8 shows, the intermediate element 70 can be slid onto one of the ring-shaped sections 22 of the sleeve 20. This allows a flat construction of the rotatable connection 1a to be realized. The first end face 76 points toward the adjusting ring 60. The radially oriented grooves 75.1 correspond to the individual teeth 64.1 of the adjusting ring 60. The grooves 74.1 or longitudinal ribs on the second end face (neither of which are illustrated) correspond to an appropriate form-fitting contour of the second part which is arranged within the sleeve 20 (not visible) and is preferably formed by the sleeve 20 itself. Longitudinally extending grooves or recesses can be made in the sleeve 20 in an easy as well as cost-effective manner, in particular more easily than radially oriented grooves.

The sleeve 20 can be designed as a cast part, for example. In this case the sleeve 20 preferably features a draft angle, particularly also in the area of the form-fitting contour of the second part which can be furnished through the sleeve 20. The draft angle is provided for removing a finished cast sleeve 20 from a mold. If the sleeve is designed as a cast part, a draft angle cannot be readily (without elaborate design measures) omitted. For compensating this mold draft, the intermediate element 70 can comprise end faces 76, 77 which are arranged toward one another at an angle α corresponding to the angle of the mold draft. In other words, the intermediate element 70 can, on one hand, make it possible for the formfitting contour of the second part to be made in the second part and in the sleeve in a simple manner. On the other hand, it can ensure a strict axial arrangement of the individual components in relation to one another even if the sleeve is designed as a cast part. The intermediate element 70 thus makes it possible for the rotatable connection to be furnished and configured in a simple and cost-effective manner, even in the case of cast sleeves.

In the exemplary embodiment shown in FIG. 7, realized on the adjusting ring 60 at an outer casing surface of the adjusting ring 60 is a lug 61 from which a counter-stop 62 protrudes in axial direction upward to the stop ring 40. The counter-stop 62 is realized as a type of pin. The stop ring 40 features on an outer casing surface of the disc-shaped segment 41 a lug 41.1 which protrudes in radial direction and forms a stop 42. Nevertheless, the components 40 and 60 in the exemplary embodiment shown in FIG. 7 can also, as a modification, be furnished according to the variants shown in FIGS. 1 through 3B. In the exemplary embodiment shown in FIG. 7, the stop ring 40 is connected in a torque-proof manner to the spindle 10. A relative rotational movement between the spindle 10 and the stop ring 40 is thereby prevented.

FIG. 8 shows that the intermediate element 70 can be slid onto a ring section 22 of the sleeve 20 before the sleeve 20 is arranged on the spindle 10. The lower (second) end face 77 on which the straight grooves running parallel to one another are arranged points toward the ring section 22. Corresponding grooves forming the form-fitting contour 54 can be provided on the ring section 22. The stop ring 40 is mounted on the spindle in such a manner that it is not only rotationally lockable, but also non-rotatably plus axially displaceable thereon. The corresponding anti-rotation means 13 is designed here as a groove realized in the outer casing surface of the spindle 10 in which the form-fitting element 43 engages.

FIGS. 9 and 10 show an arrangement of the components in which the adjusting ring 60 can be positioned at a certain rotational angle position relative to the intermediate element 70. In this case, axially displacing the intermediate element 70 is not necessarily required. The ring section 22 features an end face 22.1 for accommodating the intermediate element 70. The end face 22.1 features a cavity formed between the two ring sections. The formfitting contour 54 is realized on the end face 22.1. The ring section 22 comprises the second part. The second part is integrated into the ring section 22.

FIG. 11 illustrates a damping element 90. The damping element is a rubber element having a geometry adapted to the particular form-fitting contour. The damping element has the shape of a meander.

FIG. 12 shows an adaptable stop mechanism 30 comprising an arrangement having a spindle 10 and a sleeve 20 comparable to the arrangement shown in FIG. 3B. The damping element 90 shown in FIG. 11 is arranged between the adjusting ring 60 and the second part 50. The advantage of the arrangement between the adjusting ring 60 and the second part 50 is that it does not require a relative movement on the damping element 90. A formfitting contour 94 on the damping element 90 is formed on both end faces of the damping element 90. In both axial directions, the form-fitting contour comprises a toothed geometry with teeth 94.1 and 94.2. The form-fitting contour 94 corresponds to both the formfitting contour 54 of the second part 50 and the form-fitting contour 64 of the adjusting ring 60. The damping element 90 is arranged on the second part 50 as an inlay or on the adjusting ring 60 as a casing surrounding the form-fitting contour 54 or 64.

In one embodiment, a rotatable connection for a stand apparatus to be arranged in an operating room and including an adaptable stop mechanism which can be arranged between a first connection component and a second connection component mounted rotatably around a rotational axis relative to the first connection component and is configured to define at least two different relative rotational angles of the connection components relative to the one another or at least two different rotational ranges is provided. The adaptable stop mechanism may include a first part which can be mounted rotationally lockable on the first connection component and features at least one stop and a second part, which can be arranged non-rotatably on the second connection component. The first part may be rotatably mounted relative to the second part. The adaptable stop mechanism comprising a stop device having at least one counter-stop arranged axially between the two parts, wherein the at least one counter-stop corresponds to the at least one stop and wherein the stop device is configured to define the different relative rotational angles or rotational ranges by means of the at least one counter-stop. The invention also relates to a carrier system or a stand apparatus having such a rotatable connection.

LIST OF REFERENCE NUMERALS 1, 1a rotatable connection
10 first connection component, in particular spindle
11 groove
13 anti-rotation means, in particular radial pin or groove in outer casing surface
20 second connection component, in particular sleeve
20.2 inwardly pointing casing surface of the sleeve
21 opening for first connection component
22 ring-shaped section of the forked sleeve
22.1 end face
30 adaptable stop mechanism
40 first part, in particular stop ring
41 disc-shaped segment
41.1 lug
42 stop
42.1 side surface, in particular flat stop surface
42.2 concave or concavely curved inward inner surface
43 form-fitting element
43.1 convex or convexly curved outward outer surface
45 centering means
46 first end face, in particular sliding surface
47 second end face
50 second part, in particular toothed ring
54 form-fitting contour
54.1 individual tooth
60 stop device, in particular adjusting ring
60.1 outer casing surface
60.2 inner casing surface
61 lug
62 counter-stop
62.1 side surface, in particular flat stop surface
64 form-fitting contour
64.1 individual tooth
66 end face, in particular sliding surface
70 intermediate element
74 (first) form-fitting contour
74.1 individual groove
75 second form-fitting contour
75.1 individual groove
76 first end face
77 second end face
80 circlip
90 damping element
94 form-fitting contour
94.1 individual tooth on adjusting ring
94.2 individual tooth on second part
100 stand apparatus
101 carrier system
102 (first) carrier
R rotational axis
α angle between the two end faces of the intermediate element

The invention claimed is:

1. A rotatable connection for a stand apparatus to be arranged in an operating room and comprising an adaptable stop mechanism which can be arranged between a first connection component and a second connection component mounted rotatably around a rotational axis relative to the first connection component, the adaptable stop mechanism comprising:
a first part which can be mounted rotationally lockable on the first connection component and features at least one stop projecting axially from the first part;
a second part, which can be arranged non-rotatably on the second connection component, the first part being rotatably mounted relative to the second part;
wherein the adaptable stop mechanism comprises a stop device having at least one counter-stop arranged axially between the two parts, the at least one counter-stop being a projection extending radially outwardly from an outer casing surface of the stop device, wherein the at least one counter-stop corresponds to the at least one stop and wherein the stop device is configured to define different relative rotational angles or rotational ranges by means of the at least one counter-stop.

2. The rotatable connection according to claim 1, wherein the stop device can be positioned on one of the first part and the second part in at least two different rotational angle positions such that the stop device is non-rotatable in relation to the one of the first part and the second part.

3. The rotatable connection according to claim 1, wherein the first part is arranged such that it can be displaced along the rotational axis in an axial direction and/or the stop device is arranged such that it can be displaced along the rotational axis in the axial direction jointly with the first part.

4. The rotatable connection according to claim 1, wherein the first part and the stop device and optionally also the second part can be positioned axially on the second connection component in an axial direction.

5. The rotatable connection according to claim 1, wherein the stop device is arranged such that a non-rotatable arrangement of the stop device on the second part is ensured by weight acting on the stop device.

6. The rotatable connection according to claim 1, wherein the second part has a form-fitting contour for defining individual rotational angle positions on an inward pointing casing surface and/or on an end face pointing in an axial direction and wherein the stop device has a corresponding form-fitting contour on an end face pointing in the axial direction to the second part.

7. The rotatable connection according to claim 1, wherein the first part and the stop device together form a slide bearing.

8. The rotatable connection according to claim 1, wherein the first part comprises a sliding surface arranged on an end face pointing toward the stop device, and is configured to rotate with the sliding surface in a sliding manner and/or that the stop device comprises a sliding surface arranged on an end face pointing toward the first part and is configured to mount the first part by means of the sliding surface for a sliding rotational movement around the rotational axis, the sliding surface of the first part and/or the sliding surface of the stop device being designed as a fully continuous annular circular ring surface.

9. The rotatable connection according to claim 1, wherein the adaptable stop mechanism is configured to adjust a rotational area with a relative rotational angle between 360° and 420°.

10. The rotatable connection according to claim 1, wherein the rotatable connection comprises an intermediate element which is arranged, when viewed in an axial direction, between the first part or between the stop device, and the second connection component and at least one form-fitting contour for connection with the stop device or the second connection component, wherein a form- fitting contour is arranged on each of the two opposite lying end faces of the intermediate element.

11. The rotatable connection according to claim 1, wherein the intermediate element is designed as a ring-shaped disc, and/or the intermediate element is designed as wedge-shaped and of non-uniform axial dimension.

12. A carrier system for a stand apparatus to be arranged in an operating room and for positioning a medical technology device in the operating room comprising a rotatable connection according to claim 1 as well as the first connection component in a form of a spindle, and the second connection component in a form of a sleeve.

13. The carrier system according to claim 12, wherein the second connection component is designed as a forked sleeve, wherein at least the stop device and the second part and also the first part are arranged in between two ring-shaped segments of the forked sleeve, in one of the two ring-shaped segments, wherein the rotatable connection comprises an intermediate element which is inserted into one of the two ring-shaped segments.

14. An apparatus for arranging in an operating room and positioning a medical technology device in the operating room, comprising a rotatable connection according to claim 1.

* * * * *